United States Patent [19]

Cox et al.

[11] Patent Number: 4,457,914
[45] Date of Patent: * Jul. 3, 1984

[54] FECUNDITY OF DOMESTIC LIVESTOCK

[75] Inventors: Roinald I. Cox, Beecroft; Ronald M. Hoskinson, Normanhurst; Rex J. Scaramuzzi, Thornleigh; Patricia A. Wilson, Beacon Hill; John M. George, Armidale, all of Australia

[73] Assignee: Commonwealth Scientific and Industrial Research Organization, Campbell, Australia

[*] Notice: The portion of the term of this patent subsequent to May 25, 1999 has been disclaimed.

[21] Appl. No.: 380,325

[22] Filed: May 20, 1982

Related U.S. Application Data

[63] Continuation of Ser. No. 226,990, Jan. 21, 1981, Pat. No. 4,331,657.

[30] Foreign Application Priority Data

Feb. 6, 1980 [AU] Australia ............................... PE2274

[51] Int. Cl.$^3$ ...................... A01N 45/00; A61K 39/00
[52] U.S. Cl. ........................................ 424/88; 424/238
[58] Field of Search ................ 424/88, 238; 260/397.5

[56] References Cited

U.S. PATENT DOCUMENTS 4,123,519 10/1978 Trible et al. ........................ 424/238
4,331,657 12/1982 Cox et al. .............................. 424/88

OTHER PUBLICATIONS

R. J. Scaramuzzi et al., In Steroid Immunoassay Ed. Cameron, Hillier and Griffith, 1975, 111.
R. I. Cox et al., J. Reprod, Fertil., 1976, 46, 524.
R. J. Scaramuzzi et al., Nature 1977, 269, 817.
R. J. Scaramuzzi et al., Acta Endocrinol., 1977, 212, (Suppl) 41.
P. F. A. Van Look et al., J. Reprod. Fertil., 1978, 53, 129.
R. J. Scaramuzzi, J. Steroid Biochem., 1979, 11(1), 957.
G. B. Martin, et al., Aust. J. Expt. Agric–Anim Husb., 1979, 19, 673.
R. J. Scaramuzzi et al., J. Reprod. Fert., 1980, 58, 27.

*Primary Examiner*—Elbert L. Roberts
*Attorney, Agent, or Firm*—Millen & White

[57] ABSTRACT

A method for increasing the fecundity of a flock of female sheep or goats comprising immunizing the animals in the flock against a steroidal androgen, such as 4-androstene-3, 17-dione or testosterone, or a steroidal oestrogen, such as oestrone, as by administering an immunogenic steroid/protein conjugate to the animals, to produce a mean steroid-binding antibody titer in the flock in the range of 1 in 500 to 1 in 3000 at the start of a mating period lasting at least twice the length of the average oestrous cycle for animals in the flock, and to maintain that titer so that it does not fall outside the range 1 in 200 to 1 in 2000 at the conclusion of the mating period, the overall decline in the titer being no more than 75% during the mating period.

The antibody response to suitable immunogens is controlled by the time elapsing between primary and secondary immunizations and by the molar ratio of the steroid derivative to the protein when immunization is brought about by administration of an immunogenic steroid/protein conjugate.

16 Claims, 1 Drawing Figure

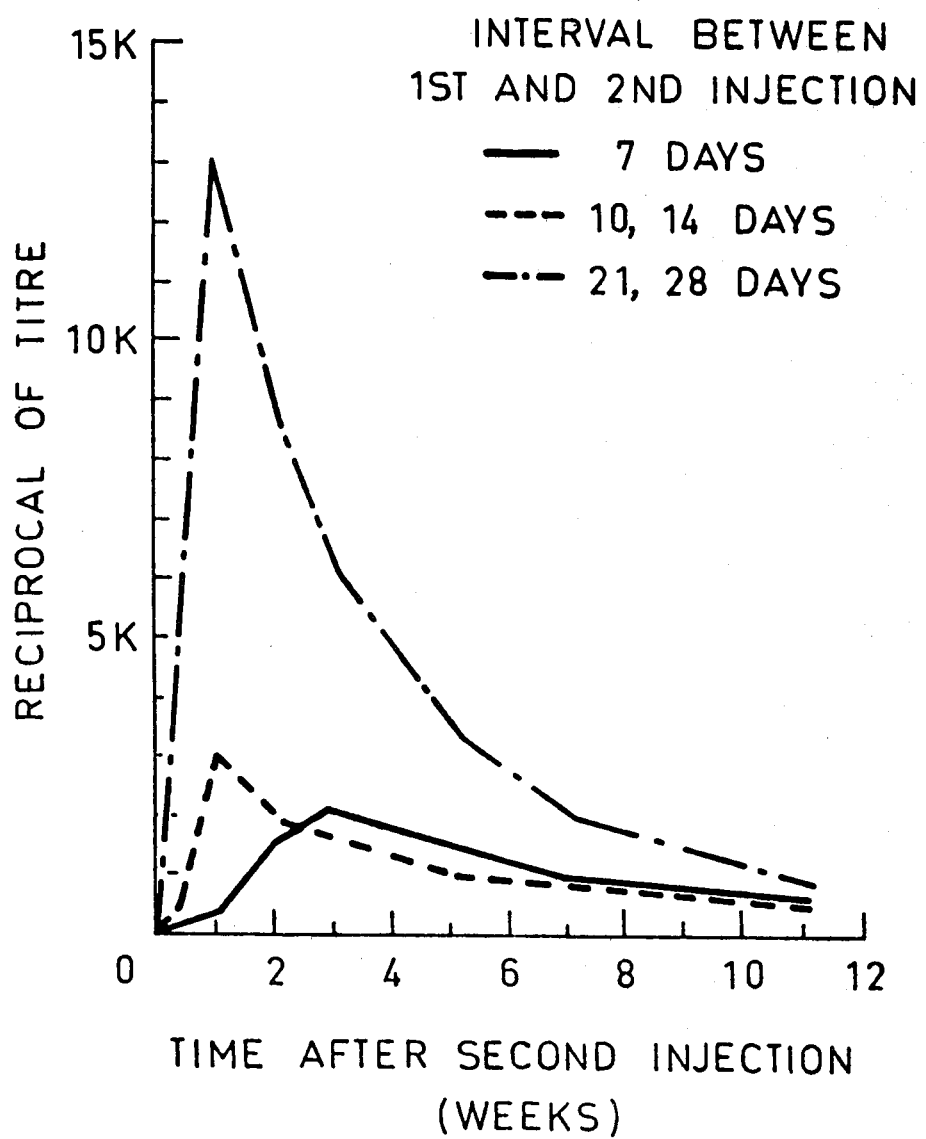

FECUNDITY OF DOMESTIC LIVESTOCK

This is a continuation of application Ser. No. 226,990 filed Jan. 21, 1981, now U.S. Pat. No. 4,331,657.

BACKGROUND OF THE INVENTION

This invention relates to methods by which the natural, genetically determined fecundity of certain livestock may be manipulated and altered. Primarily it is concerned with methods whereby individual animal fecundity of sheep or goats in a flock may be increased to a degree that signficantly exceeds natural levels. It is further concerned with substances that can bring about the biological effects of the invention and particularly the manner in which they may be used.

Because of their considerable economic importance, studies of the reproductive biology of domestic livestock have long been directed toward processes by which the fecundity of farm animals could be manipulated. In the animal production industry it is well known that there occurs from time to time within a species of sheep, for example, a strain that exhibits greater natural fecundity than others of that species. Frequently the basis for this is a genetically heritable phenomenon which, by poorly understood mechanisms, produces significantly increased multiple ovulations in animals of the more fecund strain and which is at the centre of all attempts to increase natural fecundity by animal breeding programs.

Clearly for the natural fecundity of livestock to be increased there must be at fertilization a pattern of increased ovulation rate. Though demonstration of an increased ovulation rate is a necessary requirement for increased fecundity it is by no means a sufficient determinant because of the incidence of embryo losses that may occur in a particular species throughout pregnancy.

Nevertheless, it is already known in the prior art that by artificially increasing the ovulation rate in a domestic livestock species by the administration of pregnant mare serum gonadotrophin for example, it is possible to increase the ovulation rate and ultimately the overall fecundity of the species.

In a separate prior art it was also shown that by immunization of sheep to produce antibodies directed against certain endogenous hormones, the ovulation rate of those animals could be increased. The hormones were steroids of the oestrogen and androgen classes.

SUMMARY OF THE INVENTION

The present invention consists in a method for increasing the fecundity of a flock of female sheep or goats, comprising immunizing the females in the flock against a steroidal androgen or a steroidal oestrogen, to produce a mean steroid-binding antibody titre in the flock of 1 in 500 to 1 in 3000 at the start of a mating period and to maintain that titre so that it does not exceed the range of 1 in 200 to 1 in 2000 at the conclusion of the mating period provided that the overall decline in mean steroid-binding antibody titre of the flock does not exceed 75 % during the mating period, such mating period lasting at least twice the length of the average cestrous cycle for animals in the flock.

BRIEF DESCRIPTION OF THE DRAWING

The FIGURE is a plot of antibody response as a function of the interval between primary and secondary immunizations.

DETAILED DISCUSSION

As used in this specification the following terms have the meanings set out hereunder:

Steroidal Androgen: Any steroidal substance that stimulates the expression of secodary sex characteristics of the male. Androgenic activity can be assessed by measuring the regrowth of the involuted comb of a castrated cock following androgen administration or by measuring the growth response of the seminal vesicles in castrated male rats following androgen administration.

Steroidal Oestrogen: Any steroidal substance other than oestradiol-17$\beta$ that stimulates the expression of secondary sex characteristics in the female. Oestrogenic activity can be assessed by measurement of uterine growth or cornification of the vaginal epithelium following oestrogen administration to spayed female rats or mice. Immunizations against Oestradiol-17$\beta$ have been found to render female animals anoestrous due to the neutralization of its powerful hormonal effect and it is therefore not suitable for use in the present invention.

Antibody titre: Defined here as the dilution of the antiserum which binds 50% of the maximum amount of labelled steroid bound by the antiserum during incubation of about 50 picograms of steroid for about 18 hours at 4° C. followed by the use of either dextran-coated charcoal or polyethyleneqlycol to separate free from antibody-bound steroid.

The process according to the present invention results as would be expected from the prior art, in a pattern of significantly increased ovulation rate that can be observed by enuoscopy. The process, however, surprisingly, results at mating in a pattern of significantly increased multiple fertilization occurring because, at the termination of pregnancy, the proportion of multiple births among immunized ewes for example is significantly increased, when compared with those born to a flock of unimmunized control ewes.

As a matter of practical flock management it is not possible to ensure that a given female animal is mated and fertilized in any one oestrous cycle. It is therefore an essential feature of this invention that the immunization be carried out in such a way that the desired antibody titre in the flock is maintained within the specified range for a mating period equal to at least two, and preferably three, average, osetrous cycles of the sheep.

The animals being immunised should be in moderate to good condition for age at the time of mating. The natural oestrous cycle is disturbed if animals are subjected to severe drought conditions and accordingly these animals are not susceptible to the present method.

It is preferred that the mean steroid-binding antibody titre of the flock should not fall more than 50% during the mating period. However, up to a 75% fall is acceptable provided that the titre does not fall below the minimum level for the end of the mating period.

The immunizations of the invention are performed by using conjugates of steroidal androgens and steroidal oestrogens with immunogenic proteins and in such conjugates these steroidal compounds are defined as the hapten for the purpose of this invention.

The maintenance of the average flock titre is essentially controlled by adjusting the hapten content of the immunogen i.e. the number of moles of steroid incorporated in each mole of protein conjugate and by controlling the time period elapsing between a first immunization and a booster immunization. The hapten content is from 17 to 26, and preferably from 19 to 23 moles per mole of protein when the protein is a serum albumin. However, slight variations from this range can be accommodated by varying the time period between injections of the antigen. Once a batch of antigen has been prepared it should be injected, together with a suitable adjuvant, into small numbers of test animals and the antibody titre of those test animals regularly observed over a period. This simple experimentation will reveal the appropriate spacing of injections of any given batch of antigen.

According to this invention, for example, an increase in the fecundity of domestic livestock may be achieved by immunizations using conjugates of protein and 4-androstene-3,17-dione derivatives or testosterone derivatives. The formed antibodies that are directed to the 4-androstene-3,17-dione should preferably be highly specific. In preparation of the immunogens substances already known in the art may be used. Thus preferred immunogens are prepared by the conjugation to protein of 4-androstene-3,17-dione derivatives functionalized with an acid group at positions 1, 7, 11 or 15 of the steroid ring for example. As previously stated, the critical antibody titre range that should be attained at fertilization to achieve an increase in fecundity preferably lies in the surprisingly low range of 1:500 to 1:3000 at the start of a mating period and declining to a range of 1:200 to 1:2000 at the termination of a mating period.

As this critical antibody titre range is exceeded flock fecundity declines from a maximum as a progressively greater portion of animals fail to display oestrous or ovulation in consequence of the immunization.

With mean flock antibody titres for this hormone which are significantly lower than this range the incidence of multiple ovulations will tend to diminish and flock fecundity will approach that characteristic of unimmunized animals.

As a further illustration of this invention suitable immunizations with the oestrogen, oestrone, can promote an increase in the fecundity of domestic livestock.

When the immunization is directed against oestrone there should be no substantial development of antibody populations against oestradiol-17β. This requirement determines the nature of the steroid that can best be used in forming the immunogenic steroid-protein conjugate necessary for the immunization. The preferred oestrone derivatives are those which after conjugation with protein and administration to an animal produce oestrone-specific antibody. Non-limiting examples of such oestrone derivatives already known in the art include oestrone-3-hemisuccinate, oestrone-3- carboxymethyl ether, oestrone-6-carboxymethyloxime and 15-carboxymethyloestrone.

As previously stated, in the particular case of oestrone immunizations the mean antibody titre at mating is most preferably in the range 1:500 to 1:3000 at the start of a mating period and declining to a range of 1:200 to 1:2000 at the termination of a mating period. With antibody titres for this hormone significantly lower than this range the incidence of multiple ovulations will tend to diminish. With antibody titres for this hormone significantly greater than this range an increasing proportion of animals may fail to exhibit oestrous and in both cases the overall fecundity of livestock will diminish from the maximum value attainable by immunizations producing antibody titres within the critical titre range for an effective time period.

The invention recognises that the optimum titres may vary slightly with the hormone derivative used in the immunization and with the breed of sheep being immunized.

The invention places no limitation on the protein used to form the immunizing antigen of the invention but the preferred protein is a serum albumin, typically bovine or human serum albumin. Those skilled in the art will recognise alternative protein that could be used and that to achieve the critical antibody titre ranges specified in this invention the hapten content of antigens derived from such alternative protein may vary slightly from those specified herein for the serum albumins.

In the examples given the biological effects achieved are a consequence of the development of antisteroid antibodies because immunizations of a control flocks of livestock against the protein carrier alone had no significant effect on the fecundity of the control animals. The invention is not limited to effects on sheep for like immunizations of goats to achieve the objects of the invention are similarly embraced by its concepts and processes.

The scope of this invention is not limited to processes employing active immunization protocols, for passive immunizations using homologous procedures with antisteroid antibodies formed in donor animals may be used to achieve the changes in patterns of fecundity encompassed by the invention. All the prior art immunization technologies that may be used to achieve the critical antisteroid antibody titres and the biological response of the invention are embraced by its methods and processes.

Nevertheless the invention does embrace a preferred immunization technology. To develop an antibody response to the steroid hapten of steroid-protein conjugates it is necessary to perform the immunization with such conjugates with the aid of an immunoadjuvant of which there are many well known in the art but of which Freund's complete adjuvant (FCA) is probably the best known. FCA can be used with the protein antigens embraced by the invention to produce the changes in fecundity described but in so doing it will bring about the formation of granulomatous lesions in the tissues of the immunized livestock. Such lesions diminish the commercial value of the livestock and to avoid this feature of FCA the preferred method uses diethylaminoethyldextran (DEAE dextran) to potentiate the humoral antibody responses of the invention. DEAE dextran does not produce the undesirably strong local tissue reactions that are frequently characteristic of FCA.

With immunogens prepared as described and having the composition of those described herein in association with an immunoadjuvant such as DEAE dextran, surprisingly, it is possible to obtain close control of the rate of decline of antibody titre by controlling the time elapsing between a primary and a secondary immunization. By this device it is possible to arrange the specified mean flock antibody titre ranges at mating that further decline to mean flock antibody titres below 1:50, for either oestrone or androstenedione immunizations by the time of parturition of the livestock. This result ensures that only low concentrations of steriod-binding antibody are transferred passively in the colostrum and milk to the newborn and the possibility is minimized that such passively transferred antibody could affect the post puberal reproductive performance of the offspring of immunized livestock. The figure attached illustrates in a general sense the broad effect of the interval allowed between primary and secondary immunizations on the DEAE dextran-potentiated steriod-binding antibody response to immunogenic steroid-serum albumin conjugates in sheep.

A particular feature of the preferred immunization technology of the invention is that a level of immunological memory is established in sensitized flocks such that in subsequent seasons single booster immunizations with as little as 0.4 mg immunogen can regenerate the specified mean flock antibody titre ranges at mating with attendant increases in ovulation rate and fecundity. The hapten content of immunogens used for this purpose is less critical and can vary from 15 to 30 moles steroid hapten per mole of serum albumin.

The following examples are given to illustrate preferred methods within the broad scope of this invention.

EXAMPLE 1

(a) Preparation of steroid-protein immunogen

To an amount of 200 mg 7α-carboxyethylthio-4-androstene-3,17-dione dissolved in 40 ml dioxan was added, dropwise and with stirring, a freshly prepared solution of 120 mg 1-ethyl-3(3-dimethyl aminopropyl) carbodiimide hydrochloride (ECDI) dissolved in 12 ml distilled water. The reaction was allowed to proceed for 30 minutes at 25° C. and then a solution of 300 mg human serum albumin (HSA) dissolved in 40 ml phosphate buffer pH 7.80, 0.05M was added dropwise with stirring. The reaction was allowed to continue for 20 hr and then a further 60 mg ECDI was added in solid form directly and with stirring to the mixture.

After a further 4 hr at 25° C. the reaction mixture was transferred to dialysis tubing and dialysed against distilled water. The water was changed after 2, 4, 22, 48 and 72 hr. The product (androstenedione-7α-CETE:HSA) retained in the dialysis sack was then lyophillized and weighed. Yield 320 mg.

The steroid content of the steroid-protein immunogen was calculated by incorprating a trace amount of $^3$H-7α-carboxyethylthio-4-androstene-3,17-dione in the reaction. Thus, from the specific activity of this labelled steroid derivative and of the steroid-protein immunogen, both determined by liquid scintillation counting of weighed amounts of the compounds, the Apparent Incorporation of Labelled Steroid (AILS) value was derived. In the example given a value of 25 moles steroid/mole HSA was obtained for the AILS.

In a similar preparation, oestrone-3-carboxymethyl-ether was conjugated to human serum albumen and yielded a product (Oestrone-3CM:HSA) with an AILS value of 25 moles steroid/mole HSA.

In a similar preparation, but differing in that 200 mg was used, oestrone 6-carboxymethyloxime was conjugated to human serum albumin. A product (Oestrone-6CMO:HSA) with an AILS value of 23 moles steroid/mole HSA was obtained.

In analogous preparations where the steroid hapten is reduced to 150 mg and the ECDI reagent reduced in proportion, all other reaction parameters remaining constant, a steroid-protein conjugate can be obtained with an AILS value of 17–19 moles steroid/mole HSA.

(b) Immunization of sheep to test steroid-HSA immunogen 12 mg of 4-androstene-3,17-dione-7α-CETE:HSA or oestrone 3CM:HSA immunogen was pasted in a 0.2 ml of 0.9% sterile saline and made into a total volume of 15 ml 0.9% sterile saline. Then 15 ml DEAE-dextran solution was added. The DEAE dextran solution was prepared by dissolving 15 g in 100 ml distilled water adjusting the pH to 7.5–7.7 using saturated tri-(hydroxymethyl)-methylamine buffer (500 g/liter water) and finally diluting to 150 ml with distilled water.

Four merino sheep were injected each with 3 ml of the vaccine, each sheep being given injections of about 0.9 ml intramuscularly into each hind leg and 6 injections of about 0.2 ml each into six subcutaneous sites over the dorsal region. An intramuscular injection of 0.5 ml. *B. pertussis* vaccine was also administered.

Ten to 14 days later, the same injection procedure was repeated with the immunogen in saline-DEAE dextran.

Blood samples were taken by jugular venepuncture 1, 5 and 10 weeks following the second injection treatments. Blood was collected into heparinized tubes, stored on ice and centrifuged at 40° C. The plasma so obtained was stored at −10° C. until analysis of steroid antibody titre.

The antibody titres obtained in typical tests with the 4-androstene-3,17-dione-7-αCETE:HSA and oestrone-3CM-HSA immunogens are shown in Table I.

TABLE 1

| Steroid-HSA Immunogen | Antibody Titre to Steroids (Mean values for 5 sheep per group) | | | | |
|---|---|---|---|---|---|
| | Hapten Content (Moles/Mole HSA) | Spacing of Treatment | Time of Blood Sample after Second Treatment | | |
| | | | 1 week | 5 weeks | 10 weeks |
| Androstenedione-7α-CETE:HSA | 25 | 28 days | 1:18,000 | 1:3000 | 1:1550 |
| | | 14 days | 1:3000 | 1:1100 | 1:650 |
| Oestrone-3CM:HSA | 25 | 28 days | 1:17000 | 1:2800 | 1:1200 |
| | | 14 days | 1:2500 | 1:1200 | 1:650 |
| Oestrone-6CMO:HSA | 17 | 28 days | 1:5800 | 1:1100 | 1:650 |

EXAMPLE 2

Immunisation of Merino ewes against androgen to increase ovulation rate and lambing percentage Using a pretested preparation of androstenedione-7α-CETE:HSA, a group of 50 merino ewes were immunized by the method described. A control group of 50 ewes were given injections of the vehicle, saline-DEAE dextran. The ewes were mated with rams, both the control and androstenedione-immunized animals being kept together as one flock. Mating was continued, as is common practice, for 5 weeks over the period 6–11 weeks after completion of the immunization treatment.

To obtain experimental data, but not as part of any essential procedure, the occurrence of oestrous and effective mating was observed using harnesses on the rams together with "Sire-Sine" marking crayons. Also, the ovulation rate was observed by endoscopy on the sheep within a week of oestrous being recorded. Lambs were recorded and identified with their mothers on the day of birth.

The results are shown in Table 2, indicating increased ovulation rate without loss of oestrous and increased lambing percentage in the immunized ewes as compared to the control animals.

TABLE 2

Advantageous Response of Merino Ewes to Androgen Immunization

|  | Control | 4-Androstene-3,17-dione 7-α CETE:HSA Immunized |
|---|---|---|
| Flock size | 50 | 50 |
| Flock mean androstenedione antibody titre at start of mating | Nil | 1:650 |
| Flock mean androstenedione antibody titre at end of mating | Nil | 1:209 |
| Flock ovulation rate* | 1.45 | 1.90 |
| % oestrous | 98 | 98 |
| Number of ewes lambed | 46 | 47 |
| Lambs born as: |  |  |
| (i) singles | 31 | 20 |
| (ii) twins | 30 | 54 |
| % multiple births | 32 | 57 |
| Total lambs born | 61 | 74 |

*Flock ovulation rate is defined here as the ratio of the sum of corpora lutea counted at endoscopy on the ovaries of oestrous ewes in the flock during their conception cycles and the number of corpora lutea counted on the ovaries of the non-oestrous ewes in the flock at the end of the mating period divided by the total number of ewes in the flock.

EXAMPLE 3

Immunization of Dorset Horn ewes against androgen to increase ovulation rate and lambing percentage Using a pretested preparation of 4-androstene-3,17-dione-7α-CETE:HSA a flock of 50 Dorset Horn ewes were immunized by the method described. A control group of 50 ewes were given injections of the vehicle DEAE dextran-saline.

The ewes were mated with rams in the manner described in Example 2 and both the controls and androstenedione-immunized groups were kept as one flock at pasture throughout gestation. Lambs were recorded and identified with their mothers on the day of birth.

The results showing an increase in the flock lambing rate and in the percentage of multiple births in the immunized group are shown in Table 3.

TABLE 3

Advantageous Response of Dorset Horn Ewes to Androgen Immunization

|  | Control | 4-Androstene-3,17-dione 7α-CETE:HSA Immunized |
|---|---|---|
| Flock size | 50 | 50 |
| Flock mean androstenedione antibody titre at start of mating | Nil | 1:925 |
| Flock mean androstenedione antibody titre at end of mating | Nil | 1:240 |
| Flock ovulation rate* | 1.32 | 1.70 |
| Number of mated ewes present for lambing | 46 | 42 |
| Number of ewes lambing | 36 | 35 |
| Lambing rate of ewes lambing | 1.39 | 1.57 |
| Whole flock lambing rate | 1.02 | 1.20 |
| % multiple births of ewes lambing | 39 | 55 |

EXAMPLE 4

Immunization of Merino ewes against oestrogen to increase ovulation rate and lambing percentage Using a pretested preparation of oestrone-3-carboxymethylether:HSA a flock of 49 Merino ewes were immunized by the method described. A control group of 50 ewes was kept untreated and otherwise managed identically to the immunized group. The ewes were mated with rams in the manner described in Example 2 and both controls and the oestrone-immunized group kept as one flock at pasture throughout gestation.

Lambs were recorded and identified with their mothers on the day of birth. The results showing an increase in flock lambing rate and in the percentage of multiple births in the oestrone-immunized group are shown in Table 4.

TABLE 4

Advantageous Response of Merino Ewes to Oestrogen Immunization

|  | Control | Oestrone-3CM:HSA Immunized |
|---|---|---|
| Flock size | 50 | 49 |
| Flock mean oestrone antibody titre at start of mating | Nil | 1:1803 |
| Flock mean oestrone antibody titre at end of mating | Nil | 1:1235 |
| Number of ewes anoestrous | 9 (18%) | 7 (14.3%) |
| Flock ovulation rate | 1.02 | 1.18 |
| Number of ewes lambing | 30 (60%) | 38 (77%) |
| Lambing rate of ewes lambing | 1.00 | 1.16 |
| Whole flock lambing rate | 0.6 | 0.89 |
| % multiple births of ewes lambing | 0 | 15.8% |

EXAMPLE 5

Disadvantageous response of Merino ewes to hyperimmunization against 4-androstene-3,17-dione This example is given to illustrate the disadvantageous suppression of flock fecundity that ensues when animals are immunized to such a degree that mean flock androstenedione antibody titre during mating exceeds that range specified by the invention.

A flock of 49 Merino ewes were immunized with a conjugate of 11α-hydroxy-4-androstene-3,17-dione hemisuccinate and HSA using Freund's complete adjuvant to achieve the flock mean antibody titres given in Table 5. A control group of 49 ewes and the immunized ewes were mated, with rams and managed as one flock as described in Example 2. The results in Table 5 confirm an elevated ovulation rate in the flock but diminished flock fecundity when compared with the unimmunized control flock.

TABLE 5

Disadvantageous Response of Merino Ewes to 4-Androstene-3,17-dione Hyper-immunization

| | Control | 4-Androstene-3,17-dione-11α-ol hemisuccinate: HSA Immunized |
|---|---|---|
| Flock size | 49 | 49 |
| Flock mean androstenedione antibody titre at start of mating | Nil | 1:4100 |
| Flock mean androstenedione antibody titre at end of mating | Nil | 1:3460 |
| Flock ovulation rate | 1.59 | 2.20 |
| Number of mated ewes present for lambing | 49 | 43 |
| Number not lambing | 0 | 10 |
| Lambs born to ewes present for lambing | 159% | 135% |
| Total lambs born to flock | 78 | 58 |

EXAMPLE 6

Disadvantageous response of Merino ewes to hyperimmunization against oestrone

This example is given to illustrate the disadvantageous suppression of flock fecundity that ensues when animals are immunized to such a degree that mean flock oestrone antibody titre during mating exceeds that range specified by the invention.

A flock of 24 Merino ewes were immunized repeatedly with a conjugate of oestrone-6-CMO:HSA using DEAE dextran adjuvant to achieve the flock mean antibody titres given in Table 6. A control group of 25 ewes and the immunized ewes were mated with rams and then managed as one flock as described in Example 2. The results in Table 6 confirm an elevated ovulation rate in the flock but diminished flock fecundity when compared with the unimmunized controls.

TABLE 6

Disadvantageous Response of Merino Ewes to Oestrone Hyper-immunization

| | Control | Oestrone-6-CMO:HSA Immunized |
|---|---|---|
| Flock size | 25 | 24 |
| Flock mean oestrone antibody titre at start of mating | Nil | 1:5200 |
| Flock mean oestrone antibody titre at end of mating | Nil | 1:1940 |
| Flock ovulation rate | 1.00 | 1.25 |
| Number of anoestrous ewes at mating | Nil | 7 |
| Number of ewes failing to lamb | 3 | 12 |
| Total lambs born to flock | 23 | 16 |

We claim:

1. A method for increasing the fecundity of a flock of sheep or goats, comprising immunizing the females in the flock against a steroidal androgen or a steroidal oestrogen other than oestradiol-17β prior to the start of a mating period lasting at least twice the length of the average oestrous cycle for animals in the flock, whereby steroid-binding antibodies capable of binding said steroidal androgen or oestrogen are produced in said females; and maintaining, in said females during said mating period, a level of steroid-binding antibodies sufficient to produce an increase in the fecundity of the flock.

2. A method as claimed in claim 1, wherein the steroidal androgen is a 4-androstene-3,17-dione or testosterone.

3. A method as claimed in claim 1, wherein the steroidal oestrogen is oestrone.

4. A method as claimed in claim 1, wherein the mating period is at least three times the length of the average oestrous cycle for the animals in the flock.

5. A method as claimed in claim 1, wherein the overall decline in mean steroid-binding antibody titre of the flock does not exceed 50% during the mating period.

6. A method as claimed in claim 1, wherein the mean steroid-binding antibody titre of the flock at the time of parturition is less than 1 in 50.

7. A method as claimed in claim 1, wherein the immunization is performed by stimulating antibody production with an immunogenic conjugate of the steroid androgen or oestrogen and an immunogenic protein carrier.

8. A method as claimed in claim 7, wherein the immunogenic protein human serum albumin or bovine serum albumin.

9. A method as claimed in claim 8, wherein the conjugate contains 17 to 26 moles of steroid androgen or oestrogen derivative per mole of immunogenic protein.

10. A method as claimed in claim 9, wherein the conjugate contains 19 to 23 moles of steroid androgen or oestrogen derivative per mole of immunogenic protein.

11. A method as claimed in claim 7, wherein the steroid/protein conjugate is accompanied by an immunoadjuvant.

12. A method as claimed in claim 11, wherein the immunoadjuvant is diethylaminoethyldextran.

13. A method as claimed in claim 1, wherein the immunization is brought about by passive administration of antibody raised in donor animals so as to achieve said antibody level.

14. A method as claimed in claim 7, wherein the immunogenic conjugate is a conjugate of 4-androstene-3,17-dione-7β-carboxyethylthioether and a serum albumin.

15. A method as claimed in claim 7, wherein the immunogenic conjugate is a conjugate of oestrone-3-carboxymethyl ether and a serum albumin.

16. A method as claimed in claim 1, wherein the animals are actively immunized by primary and secondary immunizations spaced apart by an interval of from 7 to 35 days.

* * * * *